United States Patent
Masuyama

(12)
(10) Patent No.: US 6,515,111 B1
(45) Date of Patent: Feb. 4, 2003

(54) MONOCLONAL ANTIBODY WHICH INHIBITS TRANSENDOTHELIAL MIGRATION OF HUMAN MONONUCLEAR LEUKOCYTES

(76) Inventor: Junichi Masuyama, 15-8, Higashijonan 4-chome, Oyama-shi, Tochigi 323-0829 (JP)

(*) Notice: Subject to any disclaimer, the term of this patent is extended or adjusted under 35 U.S.C. 154(b) by 0 days.

(21) Appl. No.: 09/508,071
(22) PCT Filed: Sep. 9, 1998
(86) PCT No.: PCT/JP98/04035
§ 371 (c)(1), (2), (4) Date: Mar. 10, 2000
(87) PCT Pub. No.: WO99/12972
PCT Pub. Date: Mar. 18, 1999

(30) Foreign Application Priority Data

Sep. 10, 1997 (JP) ............................................. 9-245203

(51) Int. Cl.[7] ................................................. C12P 21/08
(52) U.S. Cl. .............................. 530/388.75; 530/388.1; 435/326; 435/343.2
(58) Field of Search .......................... 530/388.1, 388.75; 435/326, 343.2

(56) References Cited

PUBLICATIONS

Roth et al., J. of Immunological Methods 188:97–116, 1995.*

Harlow et al., Antibodies: A Laboratory Manual, Cold Spring Harbor Publications, 1988.*

Masafumi Takahashi, et al., "Involvement of adhesion molecules in human monocyte adhesion to and transmigration through endothelial cells in vitro", Atherosclerosis, vol. 108, No. 1, pp. 73–81, 1994.

B. Naziruddin, et al., "A human endothelial–monocyte specific monoclonal antibody (SK2H10) induces intracellular Ca–2+ flux in monocytes", FASEB Journal, vol. 9, No. 3, pp. 499, 1995.

G. Zwadlo, et al., "A monoclonal antibody to a subset of human monocytes found only in the peripheral blood and inflammatory tissues", J. Immunology, vol. 137, No. 2, pp. 512–518, 1986.

\* cited by examiner

*Primary Examiner*—Patrick J. Nolan
(74) *Attorney, Agent, or Firm*—Oblon, Spivak, McClelland, Maier & Neustadt, P.C.

(57) ABSTRACT

The present invention relates to a monoclonal antibody against human mononuclear leukocytes which is capable of inhibiting transmigration of human mononuclear leukocytes after their adhesion to vascular endothelial cells, and to a hybridoma producing this antibody, and which can be used for studies to elucidate the mechanism of inflammatory reaction, and the diagnosis and therapy of inflammatory diseases.

15 Claims, 1 Drawing Sheet

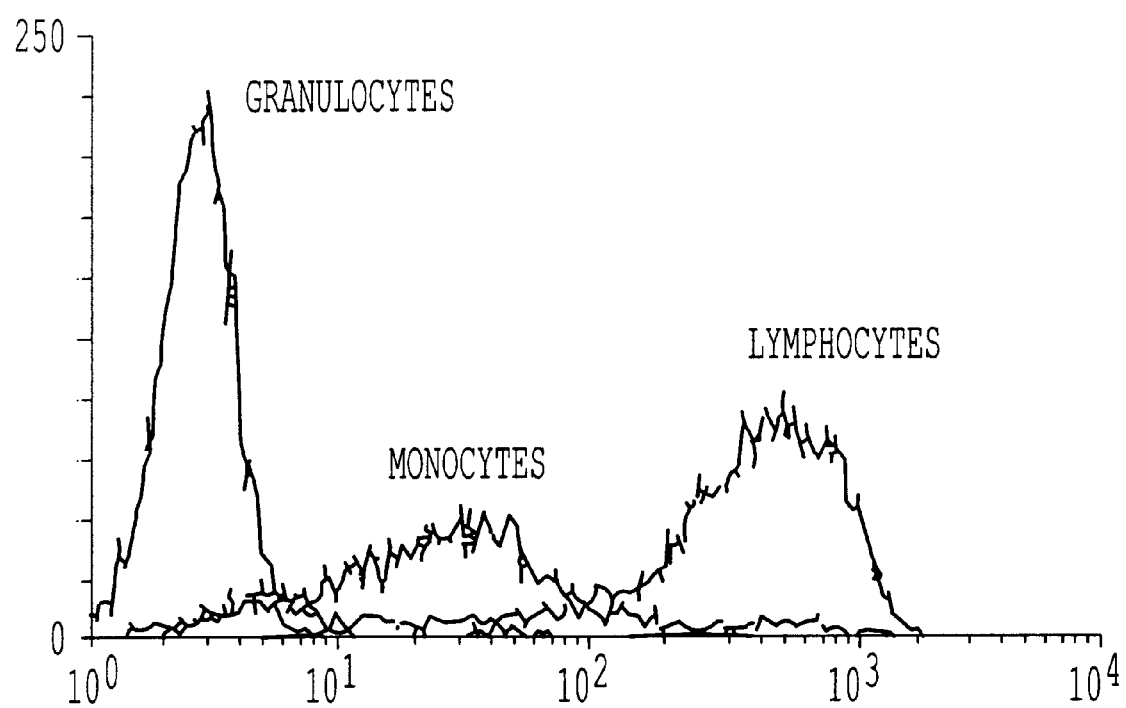

MONOCLONAL ANTIBODY WHICH INHIBITS TRANSENDOTHELIAL MIGRATION OF HUMAN MONONUCLEAR LEUKOCYTES

This application is a 371 of PCT/JP98/04035 filed on Sep. 9, 1998.

TECHNICAL FIELD

The present invention relates to a monoclonal antibody against human mononuclear leukocytes with the ability to inhibit transendothelial migration of the leukocytes in cocultures with vascular endothelial cell monolayers, said monoclonal antibody being useful for the study and treatment of inflammatory response; to a hybridoma producing this antibody.

BACKGROUND ART

Inflammatory reaction, one of the most important responses in the body defense, not only diminishes tissue damage caused by bacterial or viral infections but also promotes repair of such injured tissue. However, the inflammation often induces progressive disorders, such as autoimmune diseases or other incurable diseases of unknown cause. For the treatment of autoimmune diseases, therefore, it is essential to elucidate the mechanisms and pathological profiles of such inflammatory response. Extravasation of peripheral blood leukocytes which is observed in the earliest stage of inflammation is an important target in the therapeutic strategy for chronic inflammatory diseases.

By the use of monoclonal antibodies or molecular biological techniques, the mechanisms of leukocyte extravasation have been extensively investigated with great progress in the 1990s. At present, it is generally accepted that the process of leukocyte extravasation consists of three serial steps. Briefly, the initial step is leukocyte attachment to and rolling along the luminal surface of endothelium that is mediated by selectin. Subsequently, the leukocyte integrins are activated during this contact with the endothelial surface, by which tight adhesion of leukocytes to the endothelial cell surface occurs. The final step is the process of transendothelial migration after their tight adhesion. Although it has been hypothesized that CD31 promotes transmigration of NK cells, neutrophils, and monocytes, little is known about the molecular mechanism of transmigration of T cells which play a central role in immune reaction. Subsequent transmigration of T cells that adhered to endothelial cells is selective, but not random, as indicated by their phenotypic characteristics. Molecules that mediate the selective migration are thought to play significant roles in the onset and progression of chronic inflammatory diseases. Thus, it is important for researchers to study the nature and function of the molecules involved in the mechanisms of inflammation and the therapeutic means. For that reason monoclonal antibodies against the molecules are needed; however, thus far, there have been no such antibodies.

Accordingly, the purpose of the present invention is to provide a monoclonal antibody directed to a molecule that participates in the transmigration process (diapedesis) of human mononuclear leukocytes after their adhesion to vascular endothelial cells.

DISCLOSURE OF THE INVENTION

As a result of an extensive study for the purpose described above, the present inventor has developed a monoclonal antibody capable of inhibiting transmigration of human mononuclear leukocytes after their adhesion to vascular endothelial cells using the following methods: 1) a method of immunization with human mononuclear cells bound to human endothelial cells and migrated through human endothelial cell monolayers cultured on collagen gels into the gels below; 2) a method of screening for antibodies that inhibit transmigration of human mononuclear cells across endothelial cell monolayers cultured on collagen gels, but not their endothelial adhesion.

Thus, the present invention provides a monoclonal antibody against human mononuclear leukocytes which is capable of inhibiting transmigration of human mononuclear leukocytes after their adhesion to vascular endothelial cells.

In addition, the present invention provides a hybridoma producing the monoclonal antibody.

BRIEF DESCRIPTION OF THE DRAWING

FIG. 1 is a graph showing fluorescence intensity (reactivity with the monoclonal antibody of the present invention) of granulocytes, monocytes, and lymphocytes from a healthy donor.

BEST MODE FOR CARRYING OUT THE INVENTION

The hybridoma that produces the monoclonal antibody of the present invention can be obtained by a cell fusion method that a myeloma cell line from mammals is fused with antibody-producing cells from mammals immunized by human mononuclear leukocytes as an antigen.

As an example of mammals, mice, rabbits, rats, goats, or chickens can be used in this prevention, with mice being preferred.

The following (a) and (b) are preferably used in combination as an antigen, although human mononuclear leukocytes are generally employed: (a) human mononuclear cells that adhered to human vascular endothelial cells; (b) human mononuclear cells that migrated through human endothelial cell monolayers cultured on collagen gels into the gels below; it is particularly preferable if (a) is used as an antigen for sensitization, and (b) is used as an antigen for the final immunization. The human mononuclear cells can be obtained from peripheral blood, synovial fluids, pleural fluids, etc., with peripheral blood mononuclear cells being preferable.

Immunization may be carried out according to a standard technique. For example, mononuclear cell suspension in routinely-used buffer or saline or a mixture of the suspension and Freund's adjuvant is administered to animals intraperitoneally, subcutaneously, or through any suitable routes for the first immunization. Thereafter, a similar procedure may be repeated if necessary. For the present invention, it is preferable to perform four times or more the intraperitoneal administration of mononuclear cells mentioned in (a) and the final intravenous immunization with mononuclear cells described in (b). Although the number of mononuclear cells served as an antigen depends on administration routes and animals used, it is about 1×10' cells per mouse for each administration intraperitoneally or intravenously.

Antibody-producing cells are obtained from spleen 2–4 days after the final immunization, but lymph nodes and peripheral blood may be used instead of spleen.

Established, well-known myeloma cell lines can be used, such as P3/NS1/1-Ag4-1 (NS1), SP2/0-Ag14 (SP2), P3/x63-

Ag8 (x63), P3/x63-Ag8.U1 (P3U1), F0, MCP-11, x63.653, S194 in mice, and 210.RCY3.Ag1.2.3 (Y3) in rats.

To select hybridomas based on the ability of cell proliferation and antibody production, fused cells are cultured for several days to weeks in HAT medium.

The hybridomas obtained are screened for an antibody of interest. The screening is performed by measuring the transmigration of mononuclear cells after their adhesion to endothelial cells; hybridomas producing antibodies that inhibit the post-adhesive transmigration without interfering the adhesion are selected.

Cloning of the selected hybridomas may be performed with a limiting dilution or Sorterlone method, with the former being preferable.

The cloned hybridoma can be subcultured in ordinary medium and easily stored for a long time by being frozen in liquid nitrogen.

The monoclonal antibody of the present invention is obtained by a standard method of isolation from culture supernatants of the hybridoma or malignant ascites of animals injected with the hybridoma. The former is carried out to have highly-purified antibodies and the latter to have a large amount of antibodies.

The monoclonal antibody obtained can be further purified to the immunoglobulin fraction by a standard method with ammonium sulfate fractionation, gel filtration including DEAE cellulose column chromatography, etc.

EXAMPLE 1

(1) Preparation of Antigen

Prior to immunization, human peripheral blood mononuclear leukocytes were cocultured with human umbilical vein endothelial cells (HUVEC), and subsequently leukocytes except non-adherent leukocytes were collected to be used as an antigen. For the final immunization, mononuclear cells were used that migrated through HUVEC monolayers cultured on collagen gels 5 hr after addition to the HUVEC cultures. Briefly, HUVEC were cultured in medium containing endothelial growth supplements on Type-1 collagen gels (2 ml per dish) with a final collagen concentration of 0.8 mg/ml in 60 mm-plastic dishes. After HUVEC were grown to confluent, mononuclear cells were added to and cocultured with the HUVEC. Following an appropriate interval, HUVEC and non-migrated cells were removed from the collagen gels with 0.4% EDTA treatment, and mononuclear cells (b) migrated into the gels were released from the gels by treatment with collagenase.

(2) Immunization

Mononuclear cells (a) suspended in phosphate buffer saline (PBS) were intraperitoneally injected into mice ($1 \times 10^7$ cells per mouse). This injection was repeated 4 times or more every 2 to 4 weeks. For the final immunization, approximately $1 \times 10^7$ cells of migrated mononuclear cells were intravenously injected into the mice. Spleen was removed from the mice 2–4 days after the final immunization, and $1 \times 10^8$ spleen cells including antibody-producing cells were prepared for cell fusion with $1-2 \times 10^7$ myeloma cells that were maintained in RPMI-1640 medium containing 10% fetal calf serum (FCS).

(3) Cell Fusion

Twenty million P3/NS1/1-Ag4-1 (NS-1) cells suspended in Iscove medium were mixed with the prepared spleen cells ($1 \times 10^8$) followed by centrifugation. After suction of the supernatant, 1 ml of polyethylene glycol 4000 warmed at 37° C. was slowly dropped to the cell pellet. Subsequently, 9 ml of Iscove medium was added to the mixture. Following centrifugation, the supernatant containing polyethylene glycol was aspirated, and the spleen cells were resuspended in HAT medium plus interleukin 6 at $1 \times 10^6$/ml. One hundred microliter of the cell suspension was added to each well in 96-well flat-bottom plates and cultured at 37° C. until sufficient proliferation was achieved.

(4) Screening

A culture system to assess the post-adhesive transendothelial migration of human mononuclear leukocytes was used to screen hybridomas for the ability to produce an antibody of interest. Briefly, HUVEC monolayers were cultured on collagen gels (50 μl/well) in 96-multiwell microtiter plates according to the method described in Section (1) of Example 1. Fifty microliters of antibody supernatant and 50 μl of suspended mononuclear cells were added to each well and cultured. After a certain time, following removal of non-adherent cells, the number of adherent mononuclear cells to HUVEC in the presence of hybridoma supernatant was compared to that (control) in the absence of hybridoma supernatant under a phase contrast microscope. Compared to control wells, the wells showing no significant difference in the number of adherent cells were selected. After endothelial cells of the selected wells were removed from the collagen gel surface with 0.4% EDTA, mononuclear cells migrated into the gels were counted under a phase contrast microscope. Compared to the controls, hybridomas with the ability to suppress 50% or more of transmigration were considered to secrete the antibody of interest and selected for cloning.

(5) Cloning of Antibody-producing Hybridomas

Selected hybrid cells were cloned by limiting dilution. A hybridoma with a high suppressive ability of transmigration was chosen by recloning at least 3 times, which was considered to be the hybridoma producing the antibody of interest.

(6) Purification of Antibody

After the cloned hybridoma was grown in medium containing IL-6, the hybrid cells were intraperitoneally injected into mice which are the same strain as the hybridoma. Malignant ascites were developed and further purified to IgG by a Protein A-coupled column.

The anti-4C8 monoclonal antibody (mAb) obtained was the IgG3 class, which was deposited at the National Institute of Bioscience and Human Technology, Agency of Industrial Science and Technology, 1–3, Higashi 1-chome, Tsukuba-shi, Ibaraki-ken on Sep. 26, 2001 under the terms of the Budapest Treaty and assigned the accession number FERM BP-7757. The mAb at 1 μg/ml inhibited 80–90% of transmigration of T lymphocytes or mononuclear cells including T lymphocytes after their adhesion to HUVEC monolayers.

The anti-4C8 mAb of the present invention was characterized, with the results that are: (1) the mAb reacts with human lymphocytes, NK cells, monocytes, granulocytes including eosinophils, and adherent cells such as vascular endothelial cells; (2) the mAb changes assembly of cytoskeletal proteins such as actin polymerization; (3) the mAb has chemokine-like or chemoattractant-like activity for human lymphocytes; (4) the mAb induces attachment of human lymphocytes to the substrate; (5) the mAb increases the cell surface expression of cell activation-related antigens such as CD69; (6) the mAb reacts with granulocytes including eosinophils and and stimulates cell activation; (7) the 4C8 expression on mononuclear cells and granulocytes is decreased in patients with rheumatoid arthritis taking anti-rheumatic drugs; (8) the mAb reacts with malignant tumor cells. The methods and results of each activity are described below.

1) The Anti-4C8 mAb Reacts with Human Lymphocytes, NK Cells, Monocytes, Granulocytes Including Eosinophils, and Vascular Endothelial Cells Methods: Anti-4C8 mAb was conjugated with fluorescein by using a fluorescein labeling kit and an appropriate amount of the labeled mAb was added to 0.1 ml of peripheral whole blood with anticoagulants and incubated for 30 min on ice. After washing 3 times with cold PBS containing 0.1% bovine serum albumin (BSA), the blood cells were hemolyzed by a hemolytic reagent and fixed with paraformaldehyde. Vascular endothelial cells were removed from plastic plates with 0.4% EDTA solution, and $3 \times 10^5$ cells were stained with fluorescein-labeled anti-4C8 mAb as described above. The stained cells were analyzed for the fluorescence intensity on a flow cytometer with gating on the granulocytes, monocytes or lymphocytes.

Results: As shown in FIG. 1, although depending on individuals, the 4C8 antigen is expressed on 90% or more of lymphocytes and monocytes from healthy subjects, especially, intensely on lymphocytes and to a lesser extent on monocytes. NK cells, which comprise about 10% of lymphocytes, apparently express the 4C8 antigen. In contrast, granulocytes were almost negative for the antigen. However, the 4C8 expression on granulocytes was clearly detected in a part of patients with rheumatoid arthritis or other chronic inflammatory deseases. Similarly, the positive expression on eosinophils was observed in patients with atopic diseases. While adherent cells, such as vascular endothelial cells, did not express the 4C8 antigen in the resting and non-proliferative state, the antigen was detected in a subpopulation of proliferating endothelial cells.

2) The anti-4C8 mAb Changes Assembly of Cytoskeletal Proteins such as Actin Polymerization Methods: Wells of a 96-well flat-bottom plate were treated for 18 h at 4° C. with purified anti-4C8 mAb or control IgG3 at varying concentrations of 3–30 µg/ml. Mononuclear cells were prepared from healthy human venous blood by density gradient centrifugation. The lymphocyte fraction was obtained by passing the mononuclear cells through a nylon-wool column and suspended in RPMI-1640 medium containing 10% FCS. Lymphocytes ($3 \times 10^5$/well) were added to the wells and incubated for 1–3 hr at 37° C. After that, cells were recovered from the wells by vigorous pipetting and washed with PBS, followed by fixation with 3% paraformaldehyde. Since phalloidin binds to polymerized actin, more specifically filamentous actin, the cells treated with fluorescein-conjugated phalloidin were analyzed for the binding activity on a flow cytometer.

Results: The phalloidin-bound cells were detected in about 20% of the total lymphocytes gated by flow cytometry when stimulated with control IgG3. However, the percentage was increased up to 65% in a dose-dependent manner when stimulated with anti-4C8 mAb. Thus, stimulation of the 4C8 antigen certainly induced actin polymerization in lymphocytes.

3) The anti-4C8 mAb Stimulates Migration of Human Lymphocytes, like Chemokines

Methods: To determine whether migration of lymphocytes is induced by stimulation of the 4C8 antigen on the surface of lymphocytes, anti-4C8 mAb was used as a ligand. Lymphocytes ($3 \times 10^5$ cells/well) suspended in M199 medium without serum were added directly onto collagen gels (50 µl/well) with impregnated anti-4C8 mAb at varying concentrations in 96-multiwell plates. After a 3 hr incubation, lymphocytes adherent to the surface of the gels were removed by treatment with 0.4% EDTA, and migrated cells in the gels were counted per a field under a phase contrast microscope.

Results: The activity of anti-4C8 mAb to stimulate lymphocyte migration was detected at a concentration of 1 µg/ml, and showed up to an 8-fold increase at 10 µg/ml, compared to controls. However, the increased activity declined to the control level at 100 µg/ml. These findings indicate that the activity of anti-4C8 mAb shows a biphasic concentration-dependency as observed in chemokines or chemotactic factors. Stimulation via the 4C8 antigen clearly promotes the migratory capacity of lymphocytes.

4) The anti-4C8 mAb Stimulates Adhesion of Human Lymphocytes to the Substrate

Methods: Anti-4C8 mAb-coated plates as described in section 2) were further treated for 2 hr with 3% BSA solution. $^{51}$Cr-labeled human lymphocytes ($3 \times 10^5$ cells/well) were added to the plates. After a 1 hr incubation at 37° C., non-adherent cells were removed followed by cell lysis of adherent cells with 1N-NaOH. The radioactivity of the cells was measured by a gamma counter. The percentage of adhesion was calculated as follows: % adhesion= radioactivity of anti-4C8-coated wells—radioactivity of control wells/ radioactivity of the total added cells— radioactivity of control wells×100.

Results: Anti-4C8 mAb increased cell adhesion to the plastic plates in a dose-dependent manner ranging from 1 µg/ml to 100 µg/ml. Approximately 60% of the added cells adhered to the plates coated with 100 µg/ ml of ant-4C8 mAb, whereas the adherence was only 5% or less in the range of 1 to 100 µg/ml of control IgG3. It was evident that stimulation via the 4C8 antigen markedly increased lymphocyte adhesion to the plastic plates.

5) The Anti-4C8 mAb Induces Expression of Cell Activation-related Molecules such as CD69

Methods: Human lymphocytes were added to plates coated with anti-4C8 mAb or control IgG3 as described in section 2). After a 1 hr incubation, lymphocytes collected from the plates were stained with fluorescein-conjugated anti-CD69 mAb and analyzed for their fluorescence intensity on a flow cytometer.

Results: While only 2% of cells were positive for CD69 in cultures with control IgG3, approximately 20% of cells expressed CD69 in cultures with anti-4C8 mAb. The positivity was increased by a prolonged period of culture. Stimulation of the 4C8 antigen definitely activates lymphocytes.

6) The anti-4C8 mAb Reacts with Granulocytes Including Eosinophils, Resulting in Cell Activation Methods: The 4C8 antigen is often expressed on granulocytes from patients with rheumatoid arthritis (RA), but not healthy subjects. Whether stimulation of the 4C8 antigen activates granulocytes from such RA patients was examined. Peripheral blood was mixed with 1% dextran sulfate in the ratio of 1 to 0.75. The mixture was allowed to stand for 40–50 min, and then a granulocyte-enriched fraction was overlaid on a Ficoll-Conray solution, followed by centrifugation for 30 min. After aspiration of the supernatant, the cell pellet was washed three times with PBS at 4° C. Finally granulocytes obtained were suspended in RPMI-1640 medium. The granulocyte suspension was added to the plates coated with anti-4C8 mAb as described in section 2). Thirty minutes later, these cells were stained with fluorescein-conjugated anti-CD11b mAb which binds to activated granulocytes, and analyzed on a flow cytometer.

Results: The mean fluorescence intensity of the CD11b expression on granulocytes was significantly augmented as the concentration of coated anti-4C8 mAb increased. Thus, stimulation of the 4C8 antigen activates granulocytes.

7) Suppressive Effects of Anti-rheumatic Drugs on the 4C8 Expression of Mononuclear Cells and Granulocytes in Patients with Rheumatoid Arthritis Methods: Mononuclear cells and granulocytes were stained with fluorescein-conjugated anti-4C8 mAb. After that, lymphocytes, monocytes, and granulocytes were examined for the mean fluorescence intensity of the 4C8 expression on a flow cytometry.

Results: The 4C8 expression on mononuclear cells was low in RA patients who responded well to anti-rheumatic drugs, compared with RA patients who showed high disease activity or had never been treated. Particularly, regarding the 4C8 expression on monocytes, the fluorescence intensity level in the former patients was about 25% of that in the latter patients. The 4C8 antigen expressed on granulocytes in some of patients with active RA became almost undetectable by successful therapy with anti-rheumatic drugs. In addition to the study for the pharmacological action of anti-rheumatic drugs, assessment of the 4C8 expression on monocytes or other cells from RA patients could be clinically applicable to a means for judging or predicting the effect of such drugs.

8) The Anti-4C8 mAb Reacts with Malignant Tumor Cell Lines

Methods: SKW3 and Jurkat cells derived from malignant lymphomas were stained with fluorescein-conjugated anti-4C8 mAb, and the 4C8 expression of the cells was analyzed on a flow cytometer.

Results: The 4C8 antigen was undetected on Jurkat cells, but present on 85% of SKW3 cells. This finding indicates that some of tumor cells express the 4C8 antigen.

Industrial Applicability

At present, the mechanism of the transendothelial migration of leukocytes observed typically in inflammatory response or the mechanism of metastasis of malignant cells remains to be elucidated. However, the present invention provides a means for investigation of these mechanisms at cellular, protein, and molecular levels. In addition, since the molecule recognized by anti-4C8 mAb of the present invention is related to various pathological conditions and diseases, the mAb can be used for clinical diagnosis and therapy.

What is claimed is:

1. A monoclonal antibody specific against 4C8, which is produced by a hybridoma deposited as FERM BP-7757.

2. The monoclonal antibody of claim 1 which comprises the following properties:
   (a) the monoclonal antibody inhibits transmigration of human mononuclear leukocytes after their adhesion to vascular endothelial cells; and
   (b) the monoclonal antibody changes assembly of cytoskeletal proteins.

3. The monoclonal antibody according to claim 2, which is produced by a hybrid cell line between a myeloma cell line of animals and antibody-producing cells of animals immunized by human mononuclear cells, used as an antigen for sensitization, that adhered to human vascular endothelial cells, and further immunized by human mononuclear cells, used as an antigen for the final immunization, that migrated through human vascular endothelial cell monolayers cultured on collagen gels into the gels.

4. The hybridoma which produces the monoclonal antibody according to claim 2.

5. The hybridoma according to claim 4, which is obtained by cell fusion between a myeloma cell line of animals and antibody-producing cells of animals immunized by human mononuclear cells, used as an antigen for sensitization, that adhered to human vascular endothelial cells, and further immunized by human mononuclear cells, used as an antigen for the final immunization, that migrated through human vascular endothelial cell monolayers cultured on collagen gels into the gels.

6. A monoclonal antibody according to claim 2 wherein the antibody also has chemokine-like or chemoattractant-like activity for human lymphocytes.

7. A monoclonal antibody according to claim 2 wherein the antibody also induces attachment of human lymphocytes to a substrate upon which the antibody is attached.

8. A monoclonal antibody according to claim 2 wherein the antibody also increases the cell surface expression of a cell activation-related antigen.

9. A monoclonal antibody according to claim 2 wherein the antibody also reacts with granulocytes and stimulates cell activation.

10. A monoclonal antibody according to claim 2 wherein the antibody also causes the 4C8 expression on mononuclear cells and granulocytes to decease in patients with rheumatoid arthritis taking anti-rheumatic drugs.

11. A monoclonal antibody according to claim 2 wherein the antibody also reacts with malignant tumor cells.

12. A hybridoma which produces the monoclonal antibody of claim 1.

13. A monoclonal antibody according to claim 9 wherein the granulocytes are eosinophils.

14. A monoclonal antibody according to claim 8 wherein the cell activation-related antigen is CD69.

15. A monoclonal antibody according to claim 2 wherein the antibody induces actin polymerization in lymphocytes.

* * * * *